(12) United States Patent
Suzuki

(10) Patent No.: US 7,261,413 B2
(45) Date of Patent: Aug. 28, 2007

(54) APPARATUS FOR MEASURING FUNDUS FLUORESCENCE

(75) Inventor: Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 296 days.

(21) Appl. No.: 11/121,250

(22) Filed: May 3, 2005

(65) Prior Publication Data

US 2006/0203194 A1   Sep. 14, 2006

(30) Foreign Application Priority Data

Mar. 10, 2005   (JP) ............................. 2005-066471

(51) Int. Cl.
*A61B 3/14*   (2006.01)
*A61B 3/00*   (2006.01)

(52) U.S. Cl. ...................... 351/206; 351/205

(58) Field of Classification Search ......... 351/200–223
See application file for complete search history.

(56) References Cited

U.S. PATENT DOCUMENTS 5,504,543 A * 4/1996 Ueno ..................... 351/206
6,371,615 B1 * 4/2002 Schweitzer et al. ......... 351/221

* cited by examiner

*Primary Examiner*—Hung Dang
*Assistant Examiner*—M. Haoan
(74) *Attorney, Agent, or Firm*—Adams & Wilks

(57) ABSTRACT

Exciting light from a strobe light source is projected onto the fundus of the subject eye to excite a fluorescence substance in a subject eye fundus. Natural fluorescence exited in the fundus is received by a photodiode via a stop located at a position that is conjugate with the fundus. An XY stage is used to move the stop perpendicularly to the optical axis to change the measurement location. The output of the photodiode is used to calculate the intensity of the fluorescence from the measurement location. Since the measurement location can be changed with ease, it is possible to accurately and easily measure natural fluorescence from a desired part of the fundus.

20 Claims, 5 Drawing Sheets

APPARATUS FOR MEASURING FUNDUS FLUORESCENCE

BACKGROUND OF THE INVENTION

1. Field of the Invention

The present invention relates to an apparatus for measuring fundus fluorescence, more particularly to an apparatus for measuring natural fluorescence from the fundus of a subject eye.

2. Description of the Prior Art

Measuring fluorescence of eye tissues is used in ophthalmic diagnoses. Japanese Patent Laid Open Publication No. 1995-178055, for example, describes intravenously injecting a patient with a fluorescence agent, wherein a fundus camera is used to photograph fluorescence images in the fundus and measure the brightness of the fundus fluorescence to determine the state of the blood flow in the fundus. Japanese Patent Laid Open Publication No. 1995-8457 describes projecting exciting light onto the fundus and measuring the natural fluorescence (also called autofluorescence) given off by protein substances and oxidation degradation products, and using that as a basis for diagnosing the progression of diabetes and the like. Also, Japanese Patent Laid Open Publication No. 1997-28671 describes illuminating the cornea with exciting light, measuring the natural fluorescence coming from the cornea and using that as a non-invasive way of measuring blood glucose levels.

In age-related macular degeneration, a substance called lipofuscin accumulates in retinal macules. Lipofuscin is a type of fluorescence substance, so that it gives off natural fluorescence when illuminated with light of a specific wavelength. It is thought that measuring and grading the amount of natural fluorescence from the retina will enable early diagnosis of age-related macular degeneration.

However, the intensity of the natural fluorescence from the fundus is extremely low. In the method of Japanese Patent Laid Open Publication No. 1995-178055 in which a fundus camera is used without modification, a fluorescence agent is administered to the patient and the fluorescence from the fluorescence agent in the fundus is measured. In such a measurement it is possible to measure the fluorescence from the fluorescence agent, but impossible to measure the extremely weak natural fluorescence.

Also, to measure natural fluorescence from the fundus, exciting light is projected onto the fundus and the fluorescence has to be received via the cornea and crystalline lens, so that there is a considerable loss of intensity, and the amount of fluorescence received varies depending on the state of the eye concerned. Thus, the configuration of Japanese Patent Laid Open Publication No. 1995-8457 or No. 1997-28671 used to measure the natural fluorescence via the cornea and crystalline lens cannot be applied as-is to accurately measure the natural fluorescence from the desired portion of the fundus.

It is therefore an object of the present invention to provide an apparatus for measuring fundus fluorescence that can accurately measure natural fluorescence from a desired portion of an eye fundus.

SUMMARY OF THE INVENTION

An apparatus for measuring fundus fluorescence according to the invention comprises means for illuminating a subject eye fundus with exciting light; a light-receiving element for receiving natural fluorescence emitted from the fundus as a result of the exciting light illumination via a stop disposed at a location that is substantially conjugate with the fundus; and displacement means for changing a relative position of the stop and subject eye in a plane perpendicular to an optical axis of light received from the fundus; wherein the displacement means changes the position of the stop relative to the fundus such that the light-receiving element receives and measures natural fluorescence from a desired part of the fundus.

In accordance with the present invention, natural fluorescence from the eye fundus is received via a stop located at a position that is substantially conjugate to the fundus, and the position of the stop relative to the eye is adjusted so as to measure the natural fluorescence from a desired part of the fundus.

Furthermore, an apparatus for measuring fundus fluorescence according to the invention comprises means for illuminating an eye fundus with a beam of exciting light; scanning means for scanning the fundus with the beam of exciting light; and a light-receiving element for receiving natural fluorescence emitted from the fundus as a result of the illumination by the beam of exciting light; wherein the scanning means scan the fundus with the beam of exciting light such that the light-receiving element receives and measures natural fluorescence from a desired part of the fundus.

In the invention a laser beam is used to scan the fundus and natural fluorescence produced in the fundus by the laser beam irradiation is received and measured by the light-receiving means. This enables natural fluorescence from a desired part of the fundus to be measured because the laser beam is caused to scan a predetermined wide area of the fundus including the desired part thereof.

Further features of the invention, its nature and various advantages will be more apparent from the accompanying drawings and following detailed description of the invention.

DESCRIPTION OF THE PREFERRED EMBODIMENT

Figure 1:
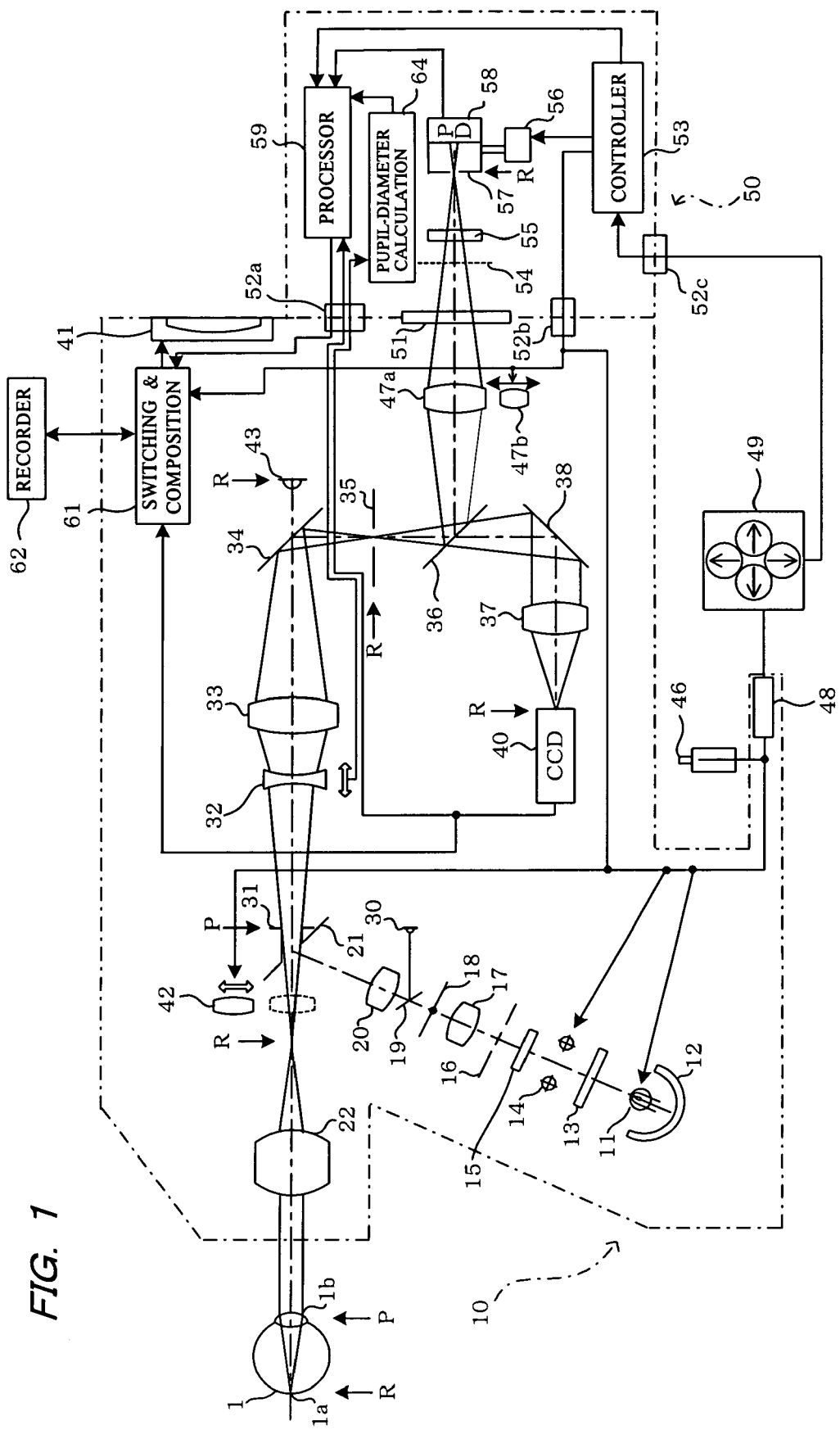
FIG. 1 is a schematic view showing the configuration of a fundus fluorescence measurement apparatus according to a first embodiment of the present invention.

FIG. 1 shows the configuration of a fundus fluorescence measurement apparatus according to a first embodiment of the invention. This apparatus comprises an optical system based on a conventional fundus camera. A mounting unit 50 can be detachably mounted to a main unit 10 by means of a mounting 51 and connectors 52a to 52c. The mounting unit 50 can be swapped for a fundus camera mounting unit (not shown) to enable the apparatus to also be used as a non-mydriatic fundus photography apparatus.

The apparatus of FIG. 1 is provided with an illumination optical system that uses observation infrared light or exciting light to illuminate a subject eye 1 to be examined. The apparatus is also provided with an optical system for forming images on a CCD or other such imaging device 40. The images are of the anterior portion 1b and fundus 1a of the subject eye 1 obtained from the reflected infrared light. The apparatus also has an optical system for receiving light falling incident on a light-receiving element constituted by a photodiode (PD) 58 that receives concentrated natural fluorescence from the fundus 1a excited by the exciting light. Constituent components from objective lens 22 to beamsplitter 36 are used by both the image-formation optical system and the light-receiving optical system. In the two optical systems, R denotes a point conjugate with the fundus 1a, and P denotes a point conjugate with the anterior portion 1b of the eye, particularly the pupil.

Figure 2:
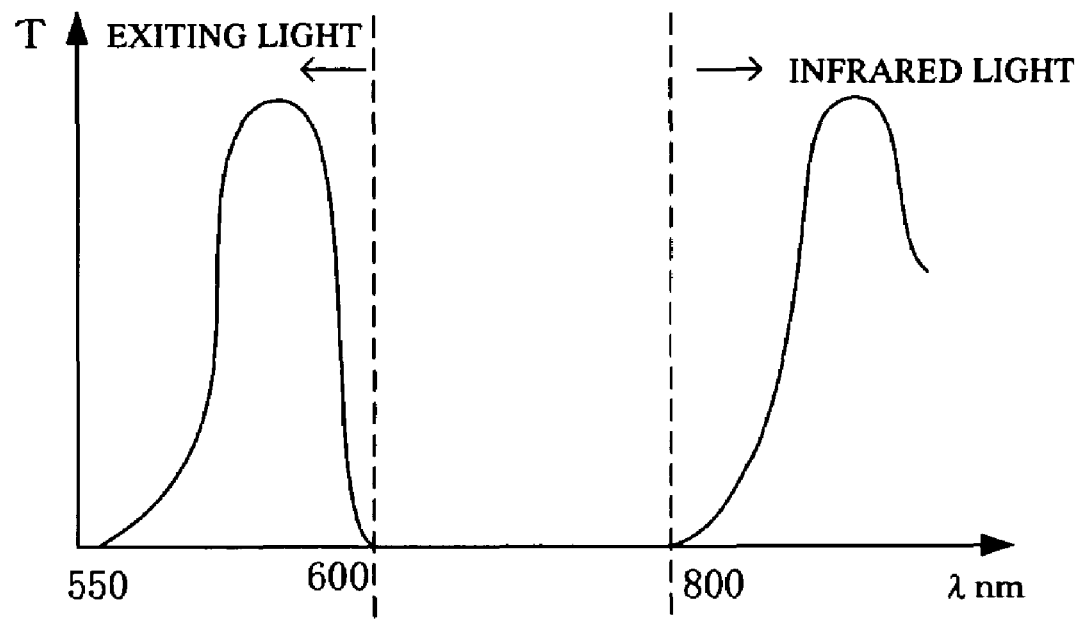
FIG. 2 is a graphical view showing the transmission characteristics of filters used in the apparatus of FIG. 1.
Figure 2:
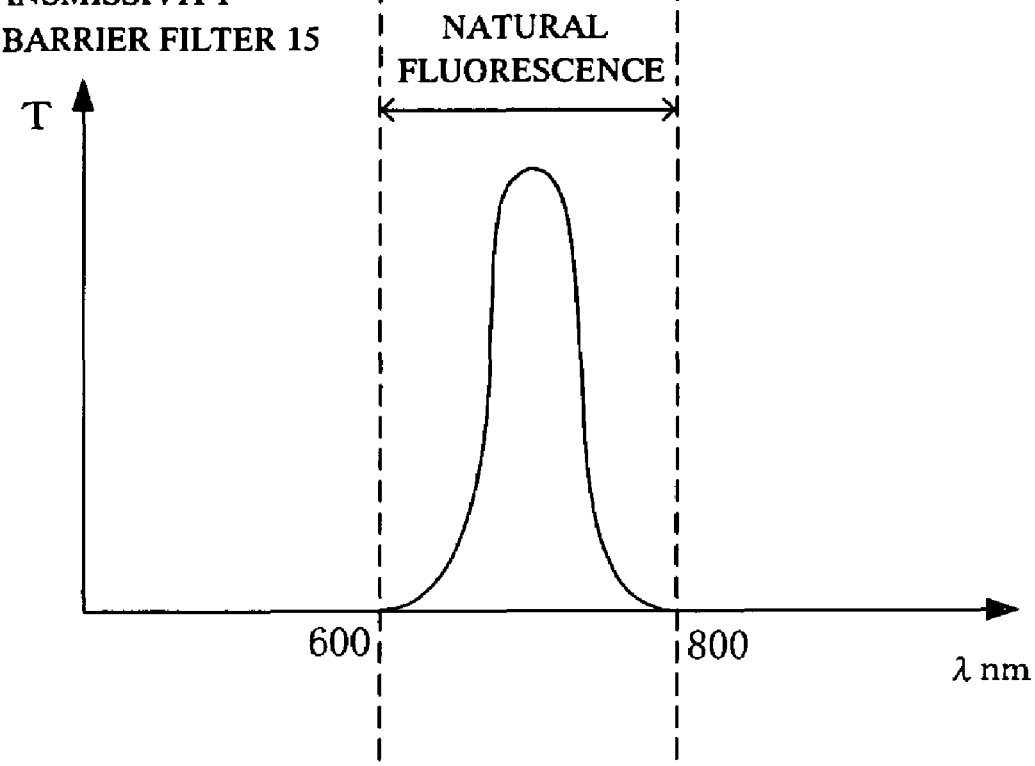

A filter 15 is located on the optical path of the illumination optical system. As shown at the upper portion in FIG. 2, the filter 15 transmits exciting light having a wavelength of from approximately 550 nm to 600 nm, and infrared light having a wavelength of approximately 800 nm and above. In this embodiment, yellow light is used for the exciting light in order to measure the natural fluorescence from deposits of lipofuscin in the fundus.

During alignment, light emitted by a lamp 11 and light reflected by a concave mirror 12 is passed through a filter 13 that blocks visible light and transmits just infrared light. The infrared light is then passed through a strobe 14 and the filter 15 and illuminates a ring-slit 16 disposed at a location conjugate with the anterior portion 1b of the eye. Illuminating light from the ring-slit 16 passes through a lens 17, a black-spot plate 18 for removing reflections from the objective lens 22, a half-mirror 19 and a relay lens 20, and is reflected by a total-reflection mirror 21 having a center aperture.

In the initial alignment step, an anterior eye lens 42 is inserted into the optical path in front of the total-reflection mirror 21. The infrared light reflected by the total-reflection mirror 21 passes through the anterior eye lens 42 and objective lens 22 and illuminates the anterior portion 1b of the eye, enabling alignment to be carried out using the anterior eye image. Once alignment has been completed at the anterior portion 1b of the eye, the anterior eye lens 42 is removed from the optical path. As a result, infrared light reflected by the total-reflection mirror 21 passes through the objective lens 22 and falls incident on the fundus 1a via the anterior portion 1b of the eye to illuminate the fundus 1a, thereby making it possible to carry out alignment using the fundus image.

Infrared light reflected from the anterior portion 1b and fundus 1a passes through the objective lens 22, the aperture in the total-reflection mirror 21, a photographic stop 31, a focus lens 32 and an image-formation lens 33, is reflected by a half-mirror 34 and, via a field stop 35 disposed at a location R conjugate with the fundus 1a, falls incident on the beamsplitter 36 that transmits infrared light and reflects visible light. Infrared light transmitted by the mirror 36 is reflected by a mirror 38, passes through an image-formation lens 37 and falls incident on an imaging device 40 constituted by an infrared CCD sensitive to infrared light.

Via the image-formation lens 37, images of the anterior portion 1b and fundus 1a carried by the infrared light are re-formed on the imaging device 40. Image signals corresponding to the images are output by the imaging device 40 and are input to a monitor 41 via a circuit 61 that switches and composes the signals, enabling the images of the anterior portion 1b and fundus 1a to be displayed on the monitor 41. The examiner can align the system while viewing the images.

Anterior eye image signals from the imaging device 40 are input to a pupil-diameter calculation unit 64, which uses the image signals to calculate the pupil diameter. The pupil-diameter calculation unit 64, controller 53 and processor 59 can be constituted by a microcomputer or ASIC or the like.

The illumination optical system is also provided with a focus-dot light source 30. A light beam from the light source 30 impinges on the subject eye 1 via the half-mirror 19. The position of the focus-dot can be adjusted by moving the focus lens 32, so that the examiner can observe the focus-dot and make adjustments to sharpen the focus on the eye. During alignment and focus operations, an internal eye fixation light 43 is on, which the examiner has the patient focus on to ensure proper alignment and focusing.

During fluorescence measurement, the filter 15 is inserted into the optical path, the shutter 54 is opened and light is emitted by the strobe 14. The filter 15 transmits exciting light from the strobe 14 along with infrared light onto the fundus 1a of the subject eye 1.

When there is an accumulation of a fluorescence substance such as lipofuscin, it emits natural fluorescence as it is excited by the exciting light. The exciting light and natural fluorescence from the fundus is reflected by the beamsplitter 36, passes through either variable-power lens 47a or variable-power lens 47b and the shutter 54, and falls incident on a barrier filter 55. The barrier filter 55 has the waveband characteristics shown in lower portion of FIG. 2 and blocks light in the exciting and infrared light wavebands, thereby transmitting only light in the natural fluorescence waveband between the wavebands of the blocked light. The natural fluorescence thus transmitted by the barrier filter 55 passes through a stop 57 and impinges on the photodiode 58, which outputs to the processor 59 a signal corresponding to the intensity of the natural fluorescence.

The stop 57 and photodiode 58 are provided as one unit and supported on an XY stage 56. The stop 57 is located in the vicinity of the photodiode 58 at a point R on the optical axis of the light-receiving optical system that is substantially conjugate with the fundus 1a. A single measurement is carried out using a single emission of strobe light from the strobe 14. The location and scope of the fundus measurement are determined by the location of the stop 57 in a plane perpendicular to the light-receiving optical axis thereof, and the size of the aperture of the stop 57.

The XY stage 56 is used to move the stop 57 and photodiode 58 in the X and Y directions in a plane perpendicular to the optical axis of the light-receiving optical system. The operation of the XY stage 56 is controlled by the controller 53 in response to input from the operation of a stage control switch 49 of the apparatus control unit 48. The examiner operates the stage control switch 49 to move the stop 57 in the X and Y directions in the plane perpendicular to the optical axis of the light-receiving optical system to thereby change the location of measurement of the fundus from which natural fluorescence is produced.

Figure 3:
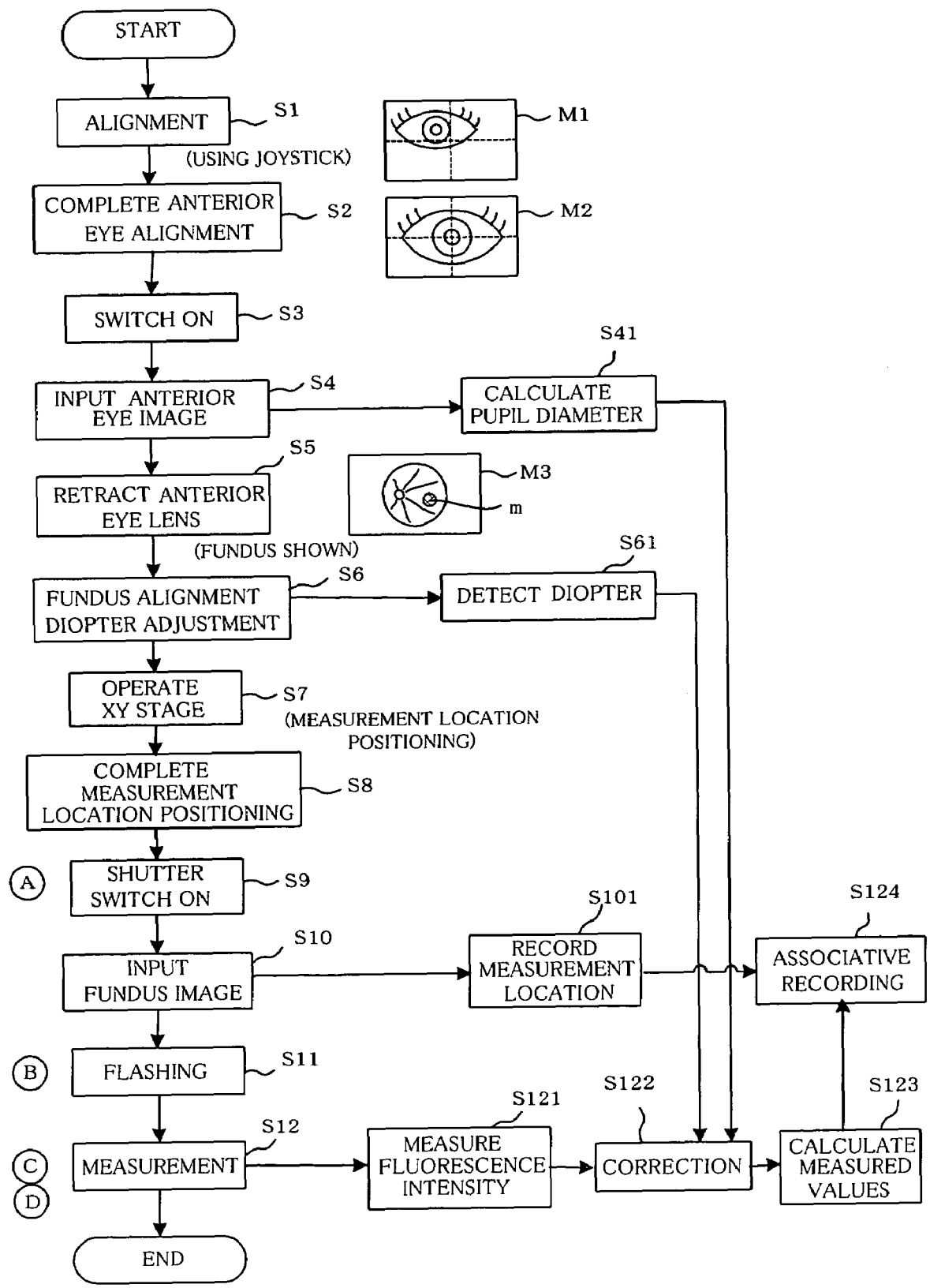
FIG. 3 is a flow chart showing the steps of the procedure for measuring fundus fluorescence using the apparatus of FIG. 1.

Next, the procedure whereby the apparatus is used to measure the natural fluorescence from the fundus will be described, with reference to the flow chart of FIG. 3.

First, the examiner operates a joystick in step S1 to move the main unit 10 relative to the subject eye 1 for coarse alignment of the system using the image of the anterior portion 1b of the eye. At this time, the lamp 11 is on and the anterior eye lens 42 is inserted into the optical path. This causes the anterior portion 1b of the subject eye 1 to be illuminated with infrared light, and light reflected from the anterior portion 1b forms its image on the imaging device 40. The image of the anterior portion 1b is displayed on the monitor 41, as denoted in FIG. 3 by the symbol M1. When the center of the pupil coincides with the center of the screen index, as shown by the symbol M2, alignment is concluded (step S2), and the examiner operates the requisite switch (not shown) on the control unit 48 (step S3).

Following this, an image of the anterior eye is input to the pupil-diameter calculation unit 64 (step S4), which calculates the pupil diameter (step S41). When this is being calculated, information relating to the position of the focus lens 32 is taken into consideration.

Directly following the input of the anterior eye image, the anterior eye lens 42 is removed from the optical path (step S5). This allows the image of the fundus 1a to be formed on the imaging device 40 and displayed on the monitor 41, as denoted in FIG. 3 by the symbol M3. The controller 53 detects the location of the stop 57. The monitor 41 shows the fundus image and the measurement location on the fundus, indicated by the symbol mark m, which is shown at a point corresponding to the detected location.

While viewing the fundus image, the examiner uses the joystick to make fine alignment with respect to the fundus, and moves the focus lens 32 to adjust the focus according to the diopter of the subject eye 1 (step S6). Here, the diopter of the eye is detected based on the position of the focus lens 32 (step S61).

Next, while observing fundus image and the measurement location mark m, the examiner moves the stop 57 by operating the stage control switch 49 to move the XY stage 56 until the mark m is at the required measurement location on the fundus image (step S7).

When measurement location positioning has been completed (step S8), the examiner switches the shutter switch 46 on (step S9). The shutter 54 then opens and the strobe 14 emits light (step S11).

Before that, fundus image data from the imaging device 40 is input to a recording unit 62 (step S10), where it is recorded as fundus measurement location data (step S101).

Any accumulation of lipofuscin in the retina of the fundus 1a will be excited by the light from the strobe 14 and emit natural fluorescence. Since the light-receiving optical system has the barrier filter 55, only natural fluorescence from the measurement location on the fundus 1a reaches the photodiode 58, which outputs to the processor 59 a signal corresponding to the intensity of the incident natural fluorescence. Based on this input signal, the processor 59 calculates the intensity of the natural fluorescence from the fundus measurement location (step S12).

Figure 4:
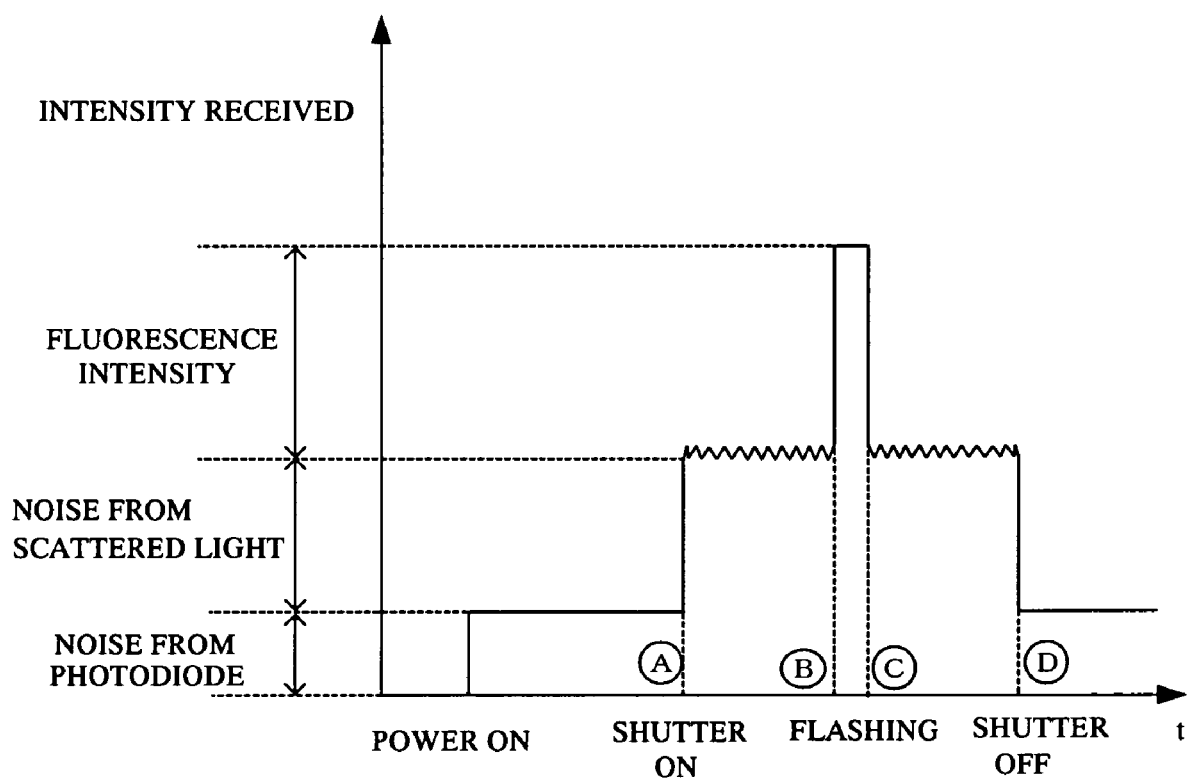
FIG. 4 is a diagram showing the waveform of the intensity of signals output by the photodiode in accordance with the operation of the shutter and the strobe in the apparatus of FIG. 1.

FIG. 4 shows the time-based changes in the output signal intensity level from the photodiode 58. When the power supply of the apparatus is switched on, the photodiode 58 outputs internal noise. When the shutter switch 46 is switched on, causing the shutter to open at time A, noise from scattered light and the like is added on. Moreover, signal components produced by the incidence of natural fluorescence between time B at which the strobe 14 lights and time C at which the strobe 14 stops emitting light are added to the output signals. From time C until the shutter 54 closes at time D, there is a fall in the signal level, as there is between times A and B. Following time D, the signal level falls further to the level prior to time A. In the natural fluorescence intensity measurement in step S12, the output signal level from the photodiode 58 prior to time B is monitored and the difference in the signal level between B and C relative to the signal level between A and B and between C and D is calculated as a component corresponding to the intensity of the natural fluorescence. The processor 59 uses this difference to calculate the fluorescence intensity as a measured value (step S121).

Furthermore, the proportion of the light emitted from the retina that passes through the anterior eye portion varies depending on the pupil diameter and diopter of the subject eye 1 at the time of the measurement. Therefore, in step S122 the processor 59 performs a correction of the measured intensity of the fluorescence calculated in step S121, based on the pupil diameter calculated in step S41 and the diopter value detected in step S61. For example, this correction decreases the measured value in inverse proportion to the pupil diameter, and decreases the measured value in accordance with an increase in the diopter on the plus side, or increases the value in accordance with an increase in the diopter on the minus side.

The final measured value of the fluorescence intensity following the correction is then calculated (step S123), and that measured value is output to, and displayed on, the monitor 41, and the measured value data is also output to the recording unit 62 where it is recorded and stored in association with the fundus image and measurement location data recorded in step S101 (step S124).

During measurement, it is desirable for the diameter of the aperture of the stop 31 to be as large as possible, so that a stop 31 with an adjustable diameter is used with its diameter being increased in synchronization with the operation of the shutter 54.

In accordance with the apparatus of this embodiment as described above, strobe 14 is used as the exciting light source, enabling the fundus to be illuminated with relatively strong exciting light. This results in a good S/N ratio, and therefore accurate measurements. In addition, the fundus measurement location can be moved by moving the stop 57 in a plane perpendicular to the light-receiving optical system axis at a position that is conjugate with the fundus, and the measurement location can be displayed on the monitor 41 together with the fundus image, making it possible for the examiner to confirm that the measurement location is the one intended. Also, only natural fluorescence from the measurement location is allowed to impinge on the photodiode 58, thereby ensuring accurate measurement of the natural fluorescence.

Moreover, the difference between the signal level during the fluorescence and the signal level immediately before and after is used to calculate the fluorescence intensity, making accurate measurements possible. Also, the diameter of the pupil of the subject eye is measured together with the diopter and the measured values are used as a basis for correcting measured fluorescence intensity values, thereby making it possible to obtain accurate measured values of fluorescence intensity.

Also, the optical system configuration is based on a conventional fundus camera, making it possible to reduce the cost of the apparatus. Also, the apparatus can be used as a fundus camera by detaching the unit 50 from the main unit 10 and affixing a fundus camera mounting unit.

In this embodiment, the stop 57 can be moved to change the measurement location on the fundus. However, instead of this, means of moving the fixation light 43 at right-angles to the optical axis can be provided to move the fixation light 43 in said direction and change the direction of the line of sight of the subject eye 1. This would make it possible to change the measurement location on the fundus 1a by moving the position of the fixation light 43 in a plane perpendicular to the optical axis of the subject eye.

This embodiment only-measures natural fluorescence emitted from lipofuscin in the fundus. However, a configuration may be used that also enables the measurement of natural fluorescence from a fluorescence substance in the fundus other than lipofuscin, using exciting light and fluorescence having different wavelengths from that of lipofuscin. In such a case, in addition to the filter 15, another filter would be provided that transmits the exciting light in the waveband that excites the other fluorescence substance and the light in the infrared waveband. Also, in addition to the barrier filter 55, a barrier filter would be provided that transmits fluorescence in the waveband emitted by the other fluorescence substance. Depending on whether the natural fluorescence to be measured is from lipofuscin or from the other substance, the natural fluorescence waveband that is transmitted can be changed by selecting either the filter 15 or the other filter, and selecting either the barrier filter 55 or the other barrier filter.

The apparatus of this embodiment has a non-mydriatic specification, and therefore can only measure one location at a time. Instead of this, an arrangement may be used in which a mydriatic agent is administered to the patient to dilate the pupil and a plurality of locations are measured in a continuous fashion, although this increases the burden on the patient. In such a case, visible light may be used for observation purposes, but it is necessary to ensure that the reflection of fluorescence by the beamsplitter 36 is not decreased. Moreover, if measurements are to be conducted on a continuous basis, it is convenient to use a program to control the XY stage 56 to move the stop 57 to the next measurement location after the completion of individual measurements at each location. Similarly, if the fixation light 43 is moved instead of the stop 57, a program can be used to control the means used to move the fixation light 43.

Figure 5:
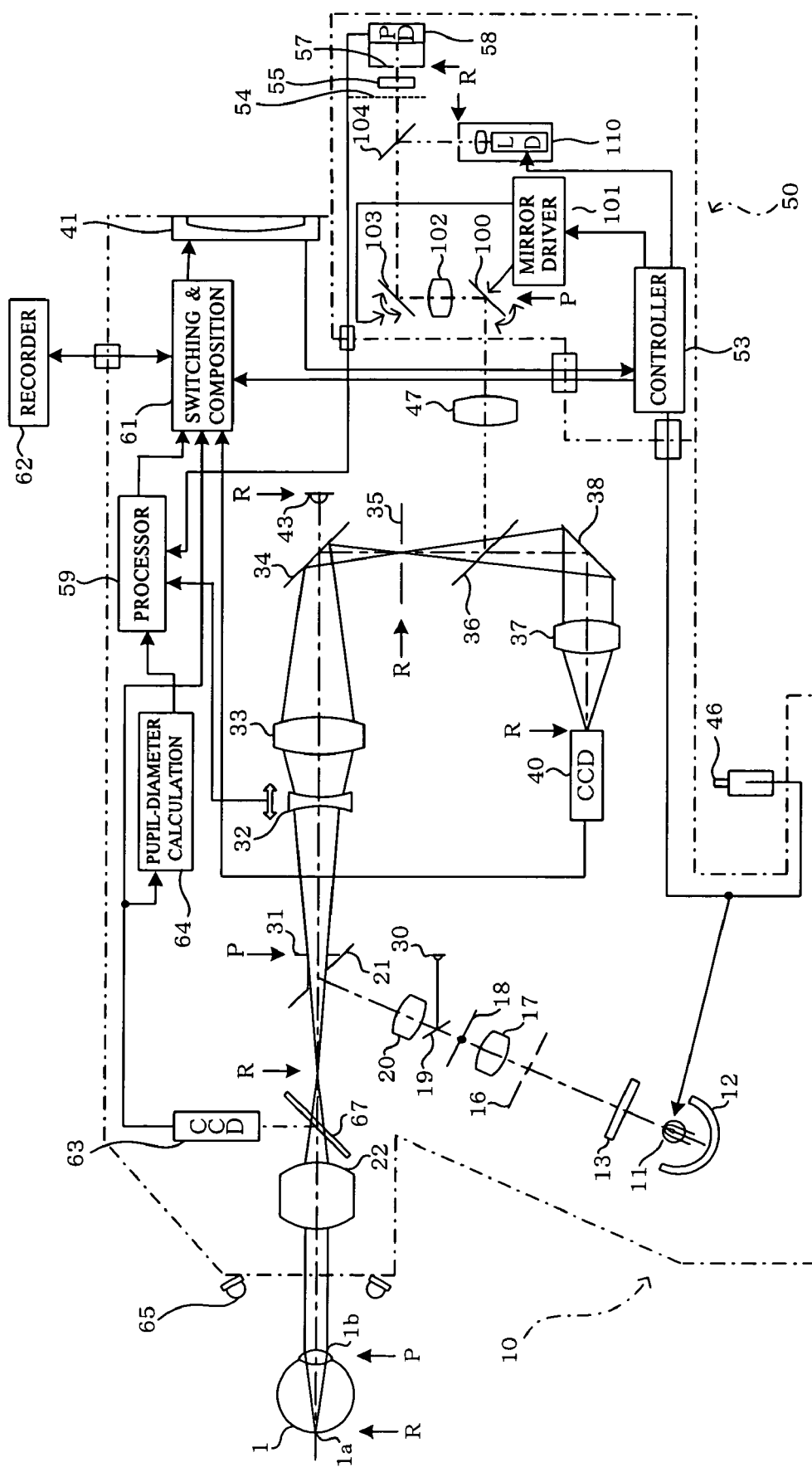
FIG. 5 is a schematic view showing the configuration of a fundus fluorescence measurement apparatus according to a second embodiment of the invention.

FIG. 5 shows the configuration of a fundus fluorescence measurement apparatus according to a second embodiment of the invention. In FIG. 5, parts that are the same or similar to parts shown in FIG. 1 are denoted using the same reference symbols, and explanation thereof is omitted.

The apparatus of this embodiment is based on scanning laser ophthalmoscope (SLO) technology. The natural fluorescence in the fundus 1a of a subject eye 1 is measured by using a scanning laser beam as the exciting light. For this, a laser diode (LD) unit 110 constituting the exciting light source is provided inside the mounting unit 50. Beamsplitter 104, scanning mirrors 100 and 103, mirror drive 101 and lens 102 are also provided in the mounting unit 50. Shutter 54, barrier filter 55, stop 57 and photodiode 58 are provided behind the beamsplitter 104.

As in the first embodiment, the stop 57 is located at a position R that is substantially conjugate with the fundus 1a, and the aperture at one end of the laser diode unit 110 from which the laser beam exits is also disposed at a position R that is conjugate with the fundus 1a. Thus, the optical system that projects the laser beam onto the fundus 1a and the optical system that direct natural fluorescence from the fundus 1a onto the photodiode 58 constitute a confocal optical system. The aperture of the stop 57 is set at a slightly larger diameter than that of the laser beam at the aperture of the laser diode unit 110.

The laser diode unit 110 comprises a laser diode that emits a laser beam having a wavelength component that excites lipofuscin, and an optical system for shaping the beam emitted from the end of the laser diode unit 110. The laser beam is reflected by the beamsplitter 104, which reflects exciting light and transmits fluorescence, and falls incident on the scanning mirror 103. The scanning mirrors 103 and 100 are driven by mirror drive 101 which swings each mirror in two dimensions (horizontally and vertically) about its center.

The laser beam reflected by the scanning mirror 103 passes through the lens 102 and is reflected through the lens 47 by the scanning mirror 100 and, via the beamsplitter 36, enters the fundus 1a of the subject eye 1. At this time, the laser beam is deflected in two dimensions about the center of the anterior portion 1b by the scanning mirrors 100 and 103 located at a point P that is conjugate with the anterior portion 1b, thereby scanning the fundus 1a in two dimensions. The range of the scanning determines the range of the measurements.

The screen of the monitor 41 is provided with a touch panel (not shown) that the examiner can use to specify the laser beam scanning range, thereby setting the measurement range. In accordance with the range thus set, the controller 53 sets the scanning angle of the scanning mirrors 100 and 103. Accordingly, the beam is deflected to scan over the specified range of the fundus 1a.

When there is an accumulation of lipofuscin in the fundus 1a, the exciting laser beam will cause the lipofuscin to fluoresce. The fluorescence passes through the beamsplitter 104 and the barrier filter 55 filters out other light components, thereby causing only natural fluorescence to pass through the stop 57 and impinge on the photodiode 58.

The beamsplitter 104 is required to have extremely difficult transmission characteristics, so that the barrier filter 55 is used to function in a supplementary manner. In an actual apparatus in FIG. 5, the scanning mirror 103 faces in a direction that is perpendicularly upwards from the plane of the drawing sheet, and the beamsplitter 104, LD unit 110, shutter 54, barrier filter 55, stop 57 and PD 58 are similarly disposed perpendicularly to the drawing sheet.

In the apparatus of this embodiment, the optical system used to illuminate and photograph the anterior portion 1b of the eye is separate from the optical system used to illuminate and photograph the fundus 1a. The front of the main unit 10 has an infrared light source 65 constituted by infrared LEDs or the like that is used to illuminate the anterior portion 1b of the eye. Light reflected from the illuminated anterior portion 1b passes through the objective lens 22 and is reflected by a half-mirror 67 that transmits visible light, and reflects half and transmits half of the infrared light. The infrared light thus reflected forms an image of the anterior portion 1b on an imaging device 63 constituted by an infrared-sensitive CCD or the like. Anterior eye image signals output from the imaging device 63 go via the switching and composition circuit 61 to be displayed on the monitor 41. The image signals are also input to the calculation unit 64, which calculates the pupil diameter. The strobe 14, filter 15 and anterior eye lens 42 of the first embodiment are omitted in the second embodiment.

With the apparatus having the above configuration, the examiner operates a joystick to move the main unit relative to the subject eye 1 for coarse alignment of the system using the image of the anterior portion 1b. At this time, the light source 65 is on, illuminating the anterior portion 1b with infrared light. The light reflected from the anterior portion 1b forms an image of the anterior eye on the imaging device 63, and signals output by the imaging device 63 are used to display the image of the anterior eye on the monitor 41. The examiner views the image as he or she carries out coarse alignment. When the alignment is finished, the examiner operates the requisite switch on the controller 53.

The lamp 11 then comes on, the fundus 1a is illuminated with infrared light and an image of the fundus 1a is formed on the imaging device 63. Also, signals output from the imaging device 63 cause the image of the anterior portion 1b displayed on the monitor 41 to be replaced by an image of the fundus 1a. The examiner views the fundus image as he or she makes fine alignment and moves the focus lens 32 to adjust the focus according to the diopter of the subject eye. The diopter is detected based on the position of the focus lens 32. During the fine alignment and diopter adjustment, anterior eye illumination and image-formation continue, and anterior eye image data from the imaging device 63 is input to the calculation unit 64 for calculation of the pupil diameter.

After completing the fine alignment and diopter adjustment, the examiner uses the monitor touch panel to specify the measurement range on the fundus 1a and then operates the shutter switch 46. As a result, the laser beam falls onto the fundus 1a, causing natural fluorescence from the portion corresponding to the beam diameter to impinge on the photodiode 58. The laser beam scans the fundus sequentially in two dimensions, so that natural fluorescence from different portions of the fundus continuously passes through the stop 57 to the photodiode 58.

The level of the signal output of the photodiode 58 changes in accordance with the timing of the shutter operation and illumination by the exciting laser beam, in basically the same way shown in FIG. 4, as described with reference to the first embodiment. That is, the difference between the output signal level of the photodiode 58 immediately before and after scanning by the laser beam and the output signal level thereof during the laser beam scanning can be thought of as the signal level produced by the natural fluorescence. Therefore, based on the level of the signal output by the photodiode 58 while the shutter 54 is open, the processor 59 uses the above difference to calculate the intensity of natural fluorescence from the measurement portion. Also, the calculated diameter of the pupil of the subject eye 1 and the detected diopter thereof are used to correct the calculated value of the natural fluorescence intensity and calculate a final measured intensity value. The measured intensity values of the fluorescence can be displayed on the monitor 41 as an intensity map, and the measurement data and fundus images are output to the recording unit 62 for associated recording and storage.

In accordance with the above apparatus of this embodiment, a laser beam that scans the fundus constitutes the exciting light, so that non-mydriatic measurement over a wide range of the fundus can be accomplished using a low amount of illumination. If there is not enough illumination, the amount of laser beam illumination has to be increased while staying within the limit that ensures the safety of the subject eye is maintained. For such cases, a configuration may be used in which the pupil is dilated to ensure the pupil diameter does not decrease.

When measuring a plurality of different locations on a continuous basis, the scanning angles of the scanning mirrors 100 and 103 are changed after each measurement to move the scanning to the next measurement area. In addition, it is possible to use a configuration that makes it possible to also measure natural fluorescence from substances in the fundus other than lipofuscin. In addition to the laser diode unit 110, such a configuration is provided with a laser diode unit that emits a laser beam in a waveband that excites the other fluorescence substance. Also, in addition to the barrier filter 55, a barrier filter is used that transmits only fluorescence in the waveband emitted by the other substance. Depending on whether the natural fluorescence to be measured is from lipofuscin or from the other substance, the appropriate laser diode unit and barrier filter are selected to measure the natural fluorescence selected.

What is claimed is:

1. An apparatus for measuring fundus fluorescence comprising:
   means for illuminating a subject eye fundus with exciting light;
   a light-receiving element for receiving natural fluorescence emitted from the fundus as a result of the exciting light illumination via a stop disposed at a location that is substantially conjugate with the fundus; and
   displacement means for changing a relative position of the stop and subject eye in a plane perpendicular to an optical axis of light received from the fundus;
   wherein the displacement means changes the position of the stop relative to the fundus such that the light-receiving element receives and measures natural fluorescence from a desired part of the fundus.

2. An apparatus according to claim 1, wherein a mean is provided that displays a measured part together with an image of the fundus.

3. An apparatus according to claim 1, wherein the displacement means changes the relative position of the stop and subject eye by moving the stop in a plane perpendicular to an optical axis of received light or by changing a position of fixation light.

4. An apparatus according to claim 1, wherein the relative position of the stop and subject eye is changed each time a measurement is carried out.

5. An apparatus according to claim 1, wherein a filter is selected through which only natural fluorescence of a specific waveband is transmitted to the light-receiving element.

6. An apparatus according to claim 1, wherein the exciting light is adjustable in wavelength.

7. An apparatus according to claim 6, wherein the wavelength of the exciting light can be adjusted according to which filter is selected.

8. An apparatus according to claim 1, wherein the exciting light is yellow light and natural fluorescence emitted by lipofuscin in the eye fundus is measured.

9. An apparatus according to claim 1, wherein natural fluorescence is measured based on a difference between signal output level of the light-receiving element during natural fluorescence incidence and signal output level of the light-receiving element immediately before and after natural fluorescence incidence.

10. An apparatus according to claim 1, wherein a measured value of natural fluorescence is corrected in accordance with subject eye diopter or subject eye pupil diameter or both thereof.

11. An apparatus according to claim 1, wherein the apparatus comprises a main unit and a mounting unit detachably mounted to the main unit and can be made to function as a fundus camera apparatus when the mounting unit is replaced with an imaging device for fundus photography.

12. An apparatus for measuring fundus fluorescence comprising:
   means for illuminating an eye fundus with a beam of exciting light;
   scanning means for scanning the fundus with the beam of exciting light; and
   a light-receiving element for receiving natural fluorescence emitted from the fundus as a result of the illumination by the beam of exciting light;

wherein the scanning means scan the fundus with the beam of exciting light such that the light-receiving element receives and measures natural fluorescence from a desired part of the fundus.

13. An apparatus according to claim 12, wherein a mean is provided that displays a measured part together with an image of the fundus.

14. An apparatus according to claim 12, wherein a filter is selected through which only natural fluorescence of a specific waveband is transmitted to the light-receiving element.

15. An apparatus according to claim 12, wherein the exciting light is adjustable in wavelength.

16. An apparatus according to claim 15, wherein the wavelength of the exciting light can be adjusted according to which filter is selected.

17. An apparatus according to claim 12, wherein the exciting light is yellow light and natural fluorescence emitted by lipofuscin in the eye fundus is measured.

18. An apparatus according to claim 12, wherein natural fluorescence is measured based on a difference between signal output level of the light-receiving element during natural fluorescence incidence and signal output level of the light-receiving element immediately before and after natural fluorescence incidence.

19. An apparatus according to claim 12, wherein a measured value of natural fluorescence is corrected in accordance with subject eye diopter or subject eye pupil diameter or both thereof.

20. An apparatus according to claim 12, wherein the apparatus comprises a main unit and a mounting unit detachably mounted to the main unit and can be made to function as a fundus camera apparatus when the mounting unit is replaced with an imaging device for fundus photography.

* * * * *